United States Patent [19]

Danklmaier

[11] Patent Number: 5,597,914
[45] Date of Patent: Jan. 28, 1997

[54] PROCESS FOR THE PRODUCTION OF CEPHALOSPORINS

[75] Inventor: Johann Danklmaier, Schwarz/Tyrol, Austria

[73] Assignee: BIOCHEMIE Gesellschaft m.b.H., Austria

[21] Appl. No.: 326,578

[22] Filed: Oct. 20, 1994

[30] Foreign Application Priority Data

Oct. 22, 1993 [AT] Austria ................ 2143/93

[51] Int. Cl.$^6$ ........................... C07D 501/18
[52] U.S. Cl. ........................... 540/230; 540/215
[58] Field of Search ................ 540/230, 215

[56] References Cited

U.S. PATENT DOCUMENTS

| | | | |
|---|---|---|---|
| 5,221,739 | 6/1993 | Wildfeuer | 540/222 |
| 5,451,675 | 9/1995 | Hiragama et al. | 540/230 |

FOREIGN PATENT DOCUMENTS

| | | |
|---|---|---|
| 0204657 | 12/1986 | European Pat. Off. . |
| 0262744 | 4/1988 | European Pat. Off. . |
| 0343926 | 11/1989 | European Pat. Off. . |
| 0442385 | 8/1991 | European Pat. Off. . |
| 0485204 | 5/1992 | European Pat. Off. . |
| 57-192392 | 11/1982 | Japan . |
| 59-163387 | 9/1984 | Japan . |
| 63-115887 | 5/1988 | Japan . |
| 1241657 | 8/1971 | United Kingdom . |
| 1241656 | 8/1971 | United Kingdom . |

OTHER PUBLICATIONS

The Journal of Antibiotics; Apr., 1992, vol. 45, No. 4 pp. 535–537.
The Journal of Organic Chemistry Mar., 1969, vol. 34, No.3—pp. 627–629.
J. Org. Chem., vol. 42, No. 10, 1977, 1801–1802.
Chem. Abstract 269883r, vol. 120, p. 1015, 1994.
Monatshëffe fur Chemie 117, 375–383 (1986).
Synlett, 1991, No. 10, Oct. , pp. 727–728.

*Primary Examiner*—John M. Ford
*Assistant Examiner*—Pavanaram K. Sripada
*Attorney, Agent, or Firm*—Robert S. Honor; Melvyn M. Kassenoff; Thomas O. McGovern

[57] ABSTRACT

A process for etherifying the hydroxymethyl group in position 3 of a cephalosporin by reaction of a 3-hydroxymethyl cephalosporin with an dioxycarbenium-tetrafluoroborate.

11 Claims, No Drawings

PROCESS FOR THE PRODUCTION OF CEPHALOSPORINS

This invention relates to a process for etherifying a hydroxymethyl group in position 3 of a cephalosporin.

Processes which are known from literature describe for example the reaction of 7-aminocephalosporanic acid (7-ACA) with an alcohol, trialkyl borate, trialkyl orthoformate or dimethoxymethan in the presence of Lewis acids. In these processes, however, the compounds of formula I are only obtained in small yields and with low purity. Also, ecologically hazardous Lewis acids are employed, often in a large excess.

In EP 0 262 744, 7-ACA or a protected form thereof is reacted with an alcohol in the presence of an excess of Lewis acids, such as $SbCl_5$, $BiCl_3$, $FeCl_3$ or $ZnCl_2$ to form 7-amino-3-alkoxymethyl-3-cephem-4-carboxylic acid. However, only low yields are obtained. The replacement of the alcohol with trialkyl borate or trialkyl orthoformate and the use of the above-mentioned catalysts only leads to a slight increase in yield (EP 0 343 926).

In the reaction of 7-ACA with $BF_3$/methanol in sulpholane, described in AT 384 222 (EP 0 204 657), a large excess of $BF_3$ and high reaction temperatures are required. Only low yields and poor quality of the 7-amino-3-methoxymethyl-3-cephem-4-carboxylic acid (7-AMCA) are obtained. Japanese patent application 63/115887 describes a variant in which the highly poisonous fluorosulphonic acid is additionally, employed, without effecting a decisive improvement in the process, however.

When using other catalysts, such as sulphuric acid, methanesulphonic acid (JP 59/163387) or trifluoromethanesulphonic acid (EP 0 442 385), the compounds of formula I are obtained in yields of only around 50%.

The reaction of protected 7-ACA derivatives is described for example in Japanese patent application 57/192392 and in DE 3,244,457. Here, the appropriately protected compounds of formula I are obtained only in moderate yields. Also, additional reaction steps are required to protect and deprotect the starting and end products. Even lower yields are obtained if a protected 3-halomethyl compound is used as the starting compound to produce the appropriately protected 3alkoxymethyl compound according to AT 303 955 (GB 1,241,657).

In AT 306 240 (GB 1,241,656), the process commences with a 7-amino-3-hydroxymethyl-3-cephem-4-carboxylic acid which is protected at the carboxylic acid group and at the amino group, and is then methylated in the presence of $BF_3$/diethyletherate at the hydroxymethyl function with diazomethane, which is hazardous for reasons of industrial safety.

It was now surprisingly found that the use of an dioxycarbenium-tetrafluoroborate for etherifying the hydroxymethyl group in position 3 of a cephalosporin overcomes the deficiencies of prior art processes. In one aspect the present invention provides therefore a process for etherifying the hydroxymethyl group in position 3 of a cephalosporin by reaction of a 3-hydroxymethyl cephalosporin with an dioxycarbenium-tetrafluoroborate. In another aspect the present invention provides a process for the production of a compound of formula

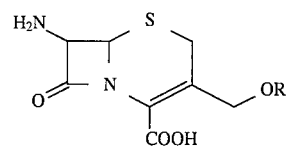

wherein R denotes alkyl or aryl, comprising reacting a compound of formula

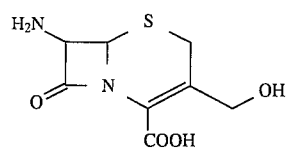

in a solvent with a compound of formula

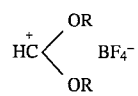

wherein R is defined as above.

The cephalosporins produced by the process of the invention are useful intermediates in the production of cephalosporins. R e.g. denotes an alkyl group, such as an $(C_{1-8})$ alkyl group, for example an $(C_{1-6})$ alkyl group, particularly the methyl or ethyl group, an alkyl group having an aromatic ring, such as a benzyl or a phenethyl group, or an aryl group, e.g. up to 10 carbon atoms such as a phenyl, tolyl, xylyl group. The groups may be unsubstituted or substituted, for example, by groups which are inert under the reaction conditions, e.g. halogen, nitro, alkoxy, alkyl therein having for example 1 to 6 carbon atoms. In one embodiment of the invention R denotes an alkyl group. In a further embodiment R is unsubstituted. Alkyl and aryl groups are for example those which have advantegous effects in cephalosporins like e.g. Cefpodoxime proxetil or the compounds mentioned in J. Antib. 45(4)(1992), p. 535 to 537.

The process according to the invention may be effected by suspending the compound of formula II in a solvent and adding a solution of the compound of formula III, which is previously isolated or is produced in situ. The temperature at this addition and during the reaction depends i.a. on the reactivity of the compound of formula III. A temperature range between −40° and +30° C. is preferred. The compound of formula III is e.g. employed in an equivalent amount, preferably, however, in an excess. For example, per mol of the starting compound of formula II 1.2 to 5 equivalents of the compound of formula III are used. The addition of the solution containing the compound of formula III may take place altogether, in several portions or continuously over several hours. In another variant of the process, the solution containing the compound of formula III may also be previously prepared, and the compound of formula II added in solid form or as a suspension.

When the reaction is complete the compound of formula I may be isolated for example by introduction of the reaction mixture into water or a mixture of water and ice, and precipitating the compound of formula I by addition of a diluted inorganic or organic base, preferably ammonia, caustic soda solution or triethylamine or by mixing the reaction mixture with an excess of an alcohol, and precipitating the compound of formula I by addition of an organic base, e.g. triethylamine and separating the precipitate, for example, by filtration.

Solvents which may be used in the production of the compounds of formula III and in the reaction with the compound of formula II may be esters of organic carboxylic acids, for example formic acid methyl ester or formic acid ethyl ester, esters of carbonic acid, for example dimethyl carbonate or dipropyl carbonate, nitroalkanes, for example nitromethane, chlorinated hydrocarbons, for example dichloromethane, as well as sulpholane, dimethyl sulphoxide or a mixture of such diluents. In one embodiment of the invention a mixture of sulpholane with formic acid methyl ester or formic acid ethyl ester is used. In a further embodiment for the introduction of an alkyl group into the compound of formula II a mixture of sulpholane with formic acid alkyl ester in which the alkyl group is identical with the alkyl group which is to be introduced is used.

Although the process has been described with respect to compounds of formula II and III it is to be appreciated that the process may be carried out with any 3-hydroxymethyl cephalosporin and dioxycarbenium tetrafluoroborate.

In the process according to the invention, the yields are considerably higher than those of processes described in literature. In addition, in contrast to processes described in literature, the reaction according to the invention may be carried out at moderate or low temperature. Thus, in particular, the formation of undesired by-products, which appear in processes described in literature and adversely affect the quality of the product or complicate the subsequent purification of the product, can be avoided by making an appropriate choice of reaction conditions. A substantial problem, for example, arising in all acid-catalysed reactions of 7-ACA is the formation of an inner lactone which lowers the quality of the product and reduces the yield. According to the process of the invention surprisingly the formation of this inner lactone is successfully suppressed. Furthermore, the process according to the invention offers essential ecological and economic advantages, since the compounds of formula III only have to be used in a slight excess and therefore only a slight excess of $BF_3$ is required.

The compounds of formula II may be produced in high yields from 7-ACA by means of chemical or enzymatic cleavage of the acetyl group, or may be prepared in a simple manner from desacetyl-cephalosporin C, after cleavage of the side chain in position 7.

Production of the compounds of formula III is described in literature, and may take place by reacting $BF_3$ with an appropriately substituted ortho-formic acid ester. For example, dimethoxycarbenium-tetrafluoroborate is obtained by reacting $BF_3$/etherate with orthoformic acid trimethyl-ester. The dimethoxycarbenium-tetrafluoroborate which is initially formed as an oil is digested several times with dichloromethane, and the desired product finally separates as a white solid substance at low temperature. Thus, the compound of formula III may be isolated as pure substance.

As described in literature on the production of dimethoxycarbenium-tetrafluoro-borate, $BF_3$ is employed as a solution in the form of the $BF_3$/diethyl etherate, among other reasons, because of its more simple handling. However, there is also the possibility of using solutions of $BF_3$ in other solvents, preferably in one of those mentioned above, and reacting them with the corresponding ortho-formic acid esters to form the compounds of formula III. If necessary, after the reaction, the compounds of formula III may be precipitated by adding an appropriate solvent, and as described in literature, purified by digesting in an appropriate solvent. Preferred solvents for precipitating and digesting are the chlorinated hydrocarbons, linear alkanes, e.g. n-hexane, or mixtures of such solvents.

In the following examples, which illustrate the invention more fully all temperatures are given in degrees celsius.

EXAMPLE 1

Production of
7-amino-3-methoxymethyl-3-cephem-4-carboxylic
acid using isolated
dimethoxycarbenium-tetrafluoroborate 20 g of 7-amino-3-hydroxymethyl-3-cephem-4-carboxylic acid are suspended in formic acid methylester and sulpholane, such that a concentration of 10% (w/v) is obtained. After cooling to −20°, 46 ml of a 5 molar solution of dimethoxycarbenium-tetrafluoroborate in formic acid methyl ester is added. Stirring is then effected for one hour at −25°. The temperature is subsequently raised to −15° and the reaction solution is stirred for 12 hours. When the reaction is complete, the reaction mixture is diluted with 300 ml of cold methanol, and the pH of the solution is set at 3.5 by adding triethylamine. The precipitated product is isolated by filtration, washed with methanol and dried in vacuo.

Yield: 16.5 g (77.8% of theory)

The proportion of 7-ACA-lactone in the product is 0.2%.

EXAMPLE 2

Production of
7-amino-3-methoxymethyl-3-cephem-4-carboxylic
acid using dimethoxycarbenium-tetrafluoroborate
produced in situ 30 g of $BF_3$/formic acid methyl ester complex are cooled to −20° and mixed with 10.5 ml of trimethyl-orthoformate. Then, a cooled suspension of 10 g of 7-amino-3- hydroxymethyl-3-cephem-4-carboxylic acid in formic acid methyl ester and sulpholane is added. The reaction solution is heated to −3° and stirred at this temperature for 12 hours, respectively, until the reaction is complete. Afterwards, the reaction solution is poured onto a mixture of ice and water, and the pH set at 3.5 by addition of aqueous ammonia. The precipitated product is isolated by filtration, washed with cold water and methanol, and dried in vacuo.

Yield: 6.5 g (61.3% of theory)

The proportion of 7-ACA-lactone in the product is 0.4%.

EXAMPLE 3

Production of
7-amino-3-ethoxymethyl-3-cephem-4-carboxylic
acid using isolated
diethoxycarbenium-tetrafluoroborate 20 g of 7-amino-3-hydroxymethyl-3-cephem-4-carboxylic acid are suspended in formic acid ethyl ester and sulpholane, such that a concentration of 11% (w/v) is obtained. After cooling to −20°, 53 ml of a 4.8 molar solution of diethoxycarbenium-tetrafluoroborate in formic acid ethyl ester are added. Then, stirring is effected for one hour at −25°, and the reaction mixture is subsequently heated to +11°. When the reaction is complete, the reaction mixture is poured onto cold water and the pH set at 3.5 by addition of aqueous ammonia. The precipitated product is isolated by filtration, washed with cold water and methanol, and dried in vacuo.

Yield: 17.7 g (79.0% of theory)

The proportion of 7-ACA-lactone in the product is 0.5%.

What I claim is:

1. In a process for the preparation of a compound of the formula

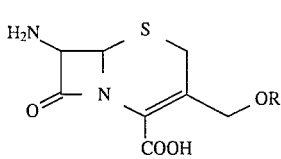

where R is alkyl, aryl, or aralkyl, by reacting a compound of the formula

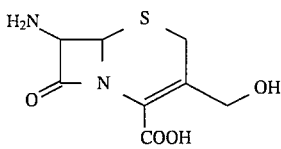

in a solvent with an etherification agent, the improvement which comprises using as the etherification agent a compound of the formula

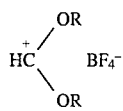

where R is as defined above.

2. A process according to claim 1, wherein R is methyl or ethyl.

3. A process according to claim 1, carried out in an ester of an organic carboxylic acid, a nitroalkane, a chlorinated hydrocarbon, sulpholane or dimethyl sulphoxide.

4. A process according to claim 1, carried out in a mixture of sulpholane and formic acid methyl ester or formic acid ethyl ester.

5. A process according to claim 1, carried out at a temperature between −40° and +30° C.

6. A process according to claim 1 in which R is $(C_{1-8})$alkyl, benzyl, phenethyl, phenyl, tolyl, or xylyl, or benzyl, phenethyl, phenyl, tolyl, or xylyl substituted with halogen, nitro, or $(C_{1-6})$alkoxy.

7. A process according to claim 1 in which R is $(C_{1-8})$alkyl.

8. A process according to claim 1 in which the reaction is carried out in formic acid methyl ester, formic acid ethyl ester, dimethyl carbonate, dipropyl carbonate, nitromethane, sulpholane, dichloromethane, dimethyl sulphoxide or a mixture thereof.

9. A process according to claim 1 in which the reaction is carried out at a temperature of −25° C. to +11° C.

10. A process according to claim 1 in which 1.2 to 5 equivalents of the compound of formula III are used per mole of the compound of formula II.

11. A process according to claim 1 in which the compound of formula III is prepared in situ by reacting $BF_3$ or a $BF_3$ complex with an R substituted orthoformic acid ester.

* * * * *